United States Patent
Duke et al.

(10) Patent No.: US 10,332,632 B2
(45) Date of Patent: Jun. 25, 2019

(54) CONTROL-TO-RANGE FAILSAFES

(71) Applicant: Roche Diabetes Care, Inc., Indianapolis, IN (US)

(72) Inventors: David L. Duke, Fishers, IN (US); Christian Ringemann, Mannheim (DE); Chinmay Uday Manohar, Fishers, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 292 days.

(21) Appl. No.: 15/170,425

(22) Filed: Jun. 1, 2016

(65) Prior Publication Data
US 2017/0348482 A1    Dec. 7, 2017

(51) Int. Cl.
| | |
|---|---|
| *A61B 5/00* | (2006.01) |
| *A61B 5/145* | (2006.01) |
| *A61M 5/142* | (2006.01) |
| *G16H 50/20* | (2018.01) |
| *G06F 19/00* | (2018.01) |
| *A61M 5/172* | (2006.01) |

(52) U.S. Cl.
CPC ......... *G16H 50/20* (2018.01); *A61B 5/14532* (2013.01); *A61B 5/4839* (2013.01); *A61M 5/14244* (2013.01); *A61M 5/1723* (2013.01); *G06F 19/3468* (2013.01); *A61M 2005/14208* (2013.01); *A61M 2005/14292* (2013.01); *A61M 2205/3303* (2013.01); *A61M 2205/50* (2013.01); *A61M 2230/201* (2013.01)

(58) Field of Classification Search
CPC .. G16H 50/20; A61B 5/14532; A61B 5/4839; A61M 5/14244; A61M 5/1723; G06F 19/00

USPC ................................................ 604/500–504
See application file for complete search history.

(56) References Cited

U.S. PATENT DOCUMENTS

| | | |
|---|---|---|
| 6,572,545 B2 | 6/2003 | Knobbe et al. |
| 6,575,905 B2 | 6/2003 | Knobbe et al. |

(Continued)

FOREIGN PATENT DOCUMENTS

| | | |
|---|---|---|
| EP | 2762073 A1 | 8/2014 |
| WO | 2002/24065 A1 | 3/2002 |

(Continued)

OTHER PUBLICATIONS

International Search Report pertaining to Appln. No. PCT/US2017/019025, filed Feb. 23, 2017, 5 pages.

(Continued)

*Primary Examiner* — Phillip A Gray
(74) *Attorney, Agent, or Firm* — Dinsmore & Shohl LLP

(57) ABSTRACT

Methods and systems are disclosed for determining a basal rate adjustment of insulin in a continuous glucose monitoring system of a person with diabetes. A method may include receiving, by at least one computing device, a signal representative of at least one glucose measurement and detecting, by the at least one computing device, a glucose state of the person based on the signal, the detected glucose state including a glucose level of the person and a rate of change of the glucose level. The method may also include calculating, by the at least one computing device, an adjustment to a basal rate of a therapy delivery device based on a control-to-range algorithm and at least one failsafe constraint to account for changes in the insulin sensitivity of the person with diabetes or inaccurate glucose measurement.

16 Claims, 9 Drawing Sheets

(56) References Cited

U.S. PATENT DOCUMENTS

| | | | |
|---|---|---|---|
| 7,291,107 | B2 | 11/2007 | Hellwig et al. |
| 7,395,158 | B2 | 7/2008 | Monfre et al. |
| 7,785,313 | B2 | 8/2010 | Mastrototaro |
| 8,579,854 | B2 | 11/2013 | Budiman et al. |
| 8,579,879 | B2 | 11/2013 | Palerm et al. |
| 8,684,922 | B2 | 4/2014 | Tran |
| 8,734,422 | B2 | 5/2014 | Hayter |
| 8,843,321 | B2 | 9/2014 | Duke et al. |
| 8,977,504 | B2 | 3/2015 | Hovorka |
| 9,247,901 | B2 | 2/2016 | Kamath et al. |
| 2002/0106709 | A1 | 8/2002 | Potts et al. |
| 2004/0167464 | A1 | 8/2004 | Ireland et al. |
| 2006/0047192 | A1 | 3/2006 | Hellwig et al. |
| 2009/0105572 | A1 | 4/2009 | Malecha |
| 2010/0262434 | A1 | 10/2010 | Shaya |
| 2011/0071464 | A1 | 3/2011 | Palerm |
| 2011/0184267 | A1 | 7/2011 | Duke et al. |
| 2011/0257627 | A1 | 10/2011 | Hovorka |
| 2011/0313674 | A1 | 12/2011 | Duke et al. |
| 2012/0165638 | A1 | 6/2012 | Duke et al. |
| 2012/0166126 | A1 | 6/2012 | Engelhardt et al. |
| 2014/0005505 | A1 | 1/2014 | Peyser et al. |
| 2014/0066884 | A1 | 3/2014 | Keenan et al. |
| 2014/0066887 | A1 | 3/2014 | Mastrototaro et al. |
| 2014/0081103 | A1 | 3/2014 | Schaible |
| 2014/0083867 | A1 | 3/2014 | Schaible |
| 2014/0088392 | A1 | 3/2014 | Bernstein et al. |
| 2014/0100435 | A1 | 4/2014 | Duke et al. |
| 2014/0118138 | A1 | 5/2014 | Cobelli et al. |
| 2014/0187887 | A1 | 7/2014 | Dunn et al. |
| 2014/0188400 | A1 | 7/2014 | Dunn et al. |
| 2014/0221966 | A1 | 8/2014 | Buckingham et al. |
| 2014/0235981 | A1 | 8/2014 | Hayter |
| 2015/0273147 | A1 | 10/2015 | Duke et al. |

FOREIGN PATENT DOCUMENTS

| | | | |
|---|---|---|---|
| WO | 2013/032965 | A1 | 3/2013 |
| WO | 2014/106263 | A2 | 7/2014 |
| WO | 2015/183689 | A1 | 3/2015 |
| WO | 2015073211 | A1 | 5/2015 |

OTHER PUBLICATIONS

Written Opinion pertaining to Appln. No. PCT/US2017/019025, filed Feb. 23, 2017, 8 pages.
International Search Report pertaining to Appln. No. PCT/US2017/019013, filed Feb. 23, 2017, 5 pages.
Written Opinion pertaining to Appln. No. PCT/US2017/019013, filed Feb. 23, 2017, 8 pages.
U.S. Non-Final Office Action dated May 31, 2018 pertaining to U.S. Appl. No. 15/170,468, 12 pages.
International Search Report pertaining to Appln. No. PCT/US2017/019030, filed Feb. 23, 2017, 5 pages.
Written Opinion pertaining to Appln. No. PCT/US2017/019030, filed Feb. 23, 2017, 9 pages.
International Search Report dated Aug. 21, 2017, pertaining to PCT/US2017/029072, filed Apr. 24, 2017, 6 pages.
Written Opinion dated Aug. 21, 2017, pertaining to PCT/US2017/029072, filed Apr. 24, 2017, 14 pages.
Jaramillo et al., Prediction of Postprandial Blood Glucose Under Intra-Patient Variability and Uncertainty and Its Use in the Design of Insulin Disposing Strategies for Type I Diabetic Patients, Jul. 22, 2011, pp. 1-178, URL:http://dugi-doc.udg.edu/bitstream/handle.
Bruno Sinopoli, et al., Kalman Filtering With Intermittent Observations, DARPA under grant F33615-01-C-1895, 28 pages.
David Di Ruscio, Closed and Open Loop Subspace System Identification of the Kalman Filter, 2009 Norwegian Society of Automatic Control, vol. 30, No. 2 , 2009, pp. 71-86, ISSN 1890-1328, Norway.
J. Zico Kolter, et al., A Probabilistic Approach to Mixed Open-loop and Closed-loop Control, with Application to Extreme Autonomous Driving, Computer Science Department, Stanford University, California (kolter@cs,stanford.edu), 7 pages, USA.
Chiara Toffanin, et al., Artificial Pancreas: Model Predictive Control Design from Clinical Experience, Journal of Diabetes Science and Technology, pp. 1470-1483, vol. 7, Issue 6, Nov. 2013, USA.
Signe Schmidt, et al., Model-Based Closed-Loop Glucose Control in Type 1 Diabetes: The DiaCon Experience, Journal of Diabetes Science and Technology, pp. 1255-1264, vol. 7, Issue 5, Sep. 2013, USA.
Schwartz et al., "Use of Automated Bolus Calculators for Diabetes Management," Diabetes Management, Touch Medical Media 2013, 92-95.
International Search Report and Written Opinion completed Jun. 10, 2016 pertaining to PCT/US2016/025502 filed Apr. 1, 2016.
Kovatchev et al., "Symmetrization of the Blood Glucose Measurement Scale and Its Applications,", Diabetes Care, 1997, vol. 20, No. 11, 1655-1658.
Lucero et al., "On the Registration of Time and the Patterning of Speech Movements," Journal of Speech, Language, and Hearing Research 40: 1111-1117.
Ward, "Hierarchical Grouping to Optimize an Objective Function," Journal of the American Statistical Association, 1963, vol. 58, Issue 301, 236-244.
Kaufman et al., Finding Groups in Data: An Introduction to Cluster Analysis (1 ed.), New York: John Wiley, ISBN 0-471-87876-6 (BOOK).
Sakoe et al., "Dynamic Programming Algorithm Optimization for Spoken Word Recognition," IEEE Transactions on Acoustics, Speech and Signal Processing 26 (1): 43-49.
Takita et al., "Cluster Analysis of Self-Monitoring Blood Glucose Assessments in Clinical Islet Cell Transplantation for Type 1 Diabetes," Diabetes Care, vol. 34, 2011, 1799-1803.
U.S. Non-Final Office Action dated Sep. 5, 2017 pertaining to U.S. Appl. No. 14/677,148, 13 Pages.
Pickup et al. (Continuous Subcutaneous Insulin Infusion at 25 Years, Diabetes Care 2002, 25, 593-598).
International Search Report pertaining to PCT application No. PCT/US2017/031661, filed May 9, 2017, 6 pages.
Written Opinion pertaining to PCT application No. PCT/US2017/031661, filed May 9, 2017, 11 pages.
Kovatchev, B.P., et al., Symmetrization of the Blood Glucose Measurement Scale and Its Applications, Diabetes American Diabetes Association, vol. 20., No. 11, Nov. 1, 1997, pp. 1655-1658, USA.
International Search Report pertaining to PCT application No. PCT/US2017/031662, filed May 9, 2017, 6 pages.
Written Opinion pertaining to PCT application No. PCT/US2017/031662, filed May 9, 2017, 9 pages.
Hughes, et al., Hypoglycemia Prevention via Pump Attenuation and Red-Yellow-Green "Traffic" Lights Using Continuous Glucose Monitoring and Insulin Pump Data, Journal of Diabetes Science and Technology, vol. 4, No. 5, Sep. 1, 2010, pp. 1146-1155, USA.

CONTROL-TO-RANGE FAILSAFES

TECHNICAL FIELD

The present invention generally relates to processing glucose data measured from a person having diabetes and, in particular, for controlling adjustment of a basal rate with a control-to-range algorithm and at least one failsafe constraint to account for changes in the insulin sensitivity of the person with diabetes or inaccurate glucose measurement.

BACKGROUND

As background, people suffer from either Type I or Type II diabetes in which the sugar level in the blood is not properly regulated by the body. Many of these people may use a continuous glucose monitoring (CGM) to monitor their glucose level on an ongoing basis. In order to perform CGM, a glucose sensor may be placed under the skin which is capable of measuring the glucose level of the person in the interstitial fluid. The glucose sensor may periodically measure the glucose level of the person at a known time interval, such as every one minute, and transmit the results of the glucose measurement result to an insulin pump, blood glucose meter, smart phone or other electronic monitor.

In some cases, the measured glucose results (from the glucose sensor) may not accurately represent the true glucose concentration. The glucose sensor may malfunction from time to time, such that the measured glucose results (from the glucose sensor) may be substantially different than the actual glucose level of the person. The glucose sensor may malfunction in this manner due to, for example, failure of the sensor electronics or battery or due to sensor "dropout." Sensor dropout may occur due to physiological problems with the glucose sensor's attachment to the person, such as movement of the sensor relative to the person. Sensor dropout may cause the measured glucose results "drop" to near zero, although the actual glucose level of the person may be much higher. Additionally, the calibration of the glucose sensor may drift resulting in a bias toward greater than the true current blood glucose level or less than the true current blood glucose level. The glucose sensor may also experience an error which causes the CGM to no longer response to changes in the true blood glucose level and remain at an incorrect artificially high or artificially low blood glucose reading.

In some cases, a person suffering from either Type I or Type II diabetes may have a change in their insulin sensitivity. When a person has a change in insulin sensitivity the CGM parameters which provided safe blood glucose stabilization may no longer be effective.

As a result, embodiments of the present disclosure may process the measured glucose results along with constraints implemented as failsafes to account for changes in the insulin sensitivity of a person with diabetes or inaccurate glucose measurement from the glucose sensor.

SUMMARY

In one embodiment, a method of determining a basal rate adjustment of insulin in a continuous glucose monitoring system of a person with diabetes is provided. The method includes receiving, by at least one computing device, a signal representative of at least one glucose measurement. The method also includes detecting, by the at least one computing device, a glucose state of the person based on the signal, the detected glucose state including a glucose level of the person and a rate of change of the glucose level. Further, the method includes calculating, by the at least one computing device, an adjustment to a basal rate of a therapy delivery device based on a control-to-range algorithm and at least one failsafe constraint to account for changes in the insulin sensitivity of the person with diabetes or inaccurate glucose measurement.

In another embodiment, a blood glucose management device configured to determine a basal rate adjustment in a continuous glucose monitoring system of a person with diabetes is provided. The device includes a non-transitory computer-readable medium storing executable instructions and at least one processing device configured to execute the executable instructions. When executed by the at least one processing device, the executable instructions cause the at least one processing device to: receive a signal representative of at least one glucose measurement; detect a glucose state of the person based on the signal, the detected glucose state including a glucose level of the person and a rate of change of the glucose level; and calculate an adjustment to a basal rate of a therapy delivery device based on a control-to-range algorithm and at least one failsafe constraints to account for changes in the insulin sensitivity of the person with diabetes or inaccurate glucose measurement.

BRIEF DESCRIPTION OF THE DRAWINGS

The embodiments set forth in the drawings are illustrative and exemplary in nature and not intended to limit the inventions defined by the claims. The following detailed description of the illustrative embodiments can be understood when read in conjunction with the following drawings, where like structure is indicated with like reference numerals and in which:

DETAILED DESCRIPTION

The embodiments described herein generally relate to methods and systems for determining a basal rate adjustment of insulin in a continuous glucose monitoring system of a person with diabetes and, in particular, for implementing at least one failsafe constraint to account for changes in the insulin sensitivity of the person with diabetes or inaccurate glucose measurement. For the purposes of defining the present disclosure, the "measured glucose results" are the glucose levels of the person as measured by the glucose sensor; the "actual glucose level" or "true glucose measurement" is the actual glucose level of the person.

Figure 1:
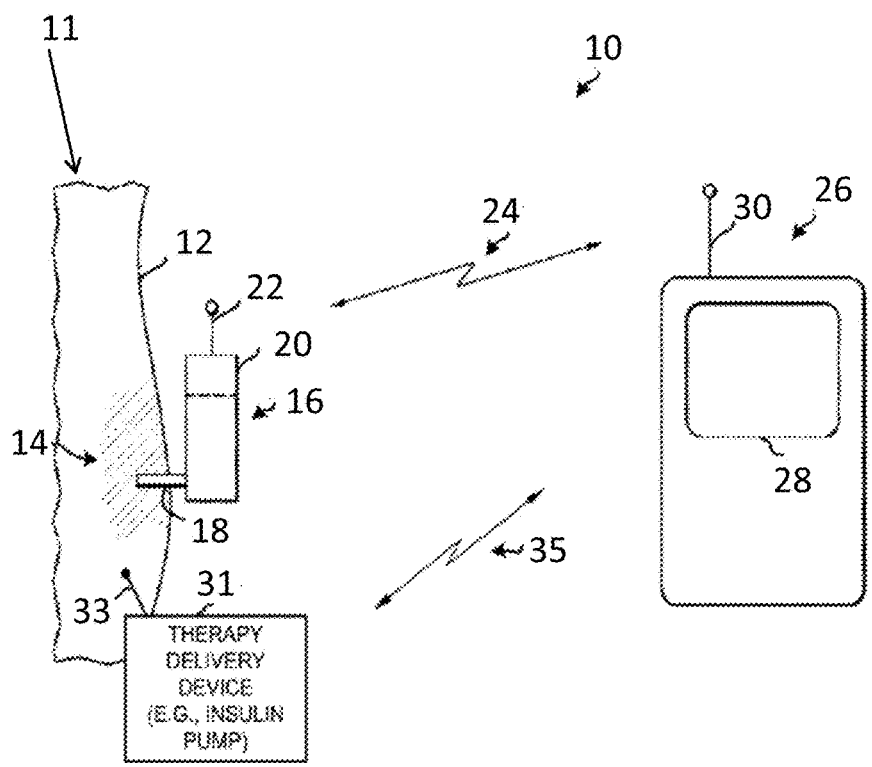
FIG. 1 illustrates a continuous glucose monitoring (CGM) system according to one or more embodiments shown and described herein.

Referring to FIG. 1, an exemplary continuous glucose monitoring (CGM) system 10 is illustrated for monitoring the glucose level of a person with diabetes (PWD) 11. In particular, CGM system 10 is operative to collect a measured glucose value at a predetermined, adjustable interval, such as every one minute, five minutes, or at other suitable intervals. CGM system 10 illustratively includes a glucose sensor 16 having a needle or probe 18 that is inserted under the skin 12 of the person. The end of the needle 18 is positioned in interstitial fluid 14, such as blood or another bodily fluid, such that measurements taken by glucose sensor 16 are based on the level of glucose in interstitial fluid 14. Glucose sensor 16 is positioned adjacent the abdomen of the person or at another suitable location. Furthermore, the glucose sensor 16 may be periodically calibrated in order to improve its accuracy. This periodic calibration may help correct for sensor drift due to sensor degradation and changes in the physiological condition of the sensor insertion site. Glucose sensor 16 may comprise other components as well, including but not limited to a wireless transmitter 20 and an antenna 22. Glucose sensor 16 may alternatively use other suitable devices for taking measurements, such as, for example, a non-invasive device (e.g., infrared light sensor). Upon taking a measurement, glucose sensor 16 transmits the measured glucose value via a communication link 24 to a computing device 26, illustratively a blood glucose (bG) management device 26. The bG management device 26 may also be configured to store in memory 39 a plurality of measured glucose results received from the glucose sensor 16 over a period of time.

CGM system 10 further includes a therapy delivery device 31, illustratively an insulin infusion pump 31, for delivering therapy (e.g., insulin) to the person. Insulin pump 31 is in communication with management device 26 via a communication link 35, and management device 26 is able to communicate bolus and basal rate information to insulin pump 31. Insulin pump 31 includes a catheter 33 having a needle that is inserted through the skin 12 of the person 11 for injecting the insulin. Insulin pump 31 is illustratively positioned adjacent the abdomen of the person or at another suitable location. Similar to glucose sensor 16, infusion pump 31 also includes a wireless transmitter and an antenna for communication with management device 26. Insulin pump 31 is operative to deliver basal insulin (e.g., small doses of insulin continuously or repeatedly released at a basal rate) and bolus insulin (e.g., a surge dose of insulin, such as around a meal event, for example). The bolus insulin may be delivered in response to a user input triggered by the user, or in response to a command from management device 26. Similarly, the basal rate of the basal insulin is set based on user input or in response to a command from management device 26. Infusion pump 31 may include a display for displaying pump data and a user interface providing user controls. In an alternative embodiment, insulin pump 31 and glucose sensor 16 may be provided as a single device worn by the patient, and at least a portion of the logic provided by processor or microcontroller may reside on this single device. Bolus insulin may also be injected by other means, such as manually by the user via a needle.

In one embodiment, such a CGM system 10 is referred to as an artificial pancreas system that provides closed loop or semi-closed loop therapy to the patient to approach or mimic the natural functions of a healthy pancreas. In such a system, insulin doses are calculated based on the CGM readings and are automatically delivered to the patient based on the CGM reading. For example, if the CGM indicates that the user has a high blood glucose level or hyperglycemia, the system can calculate an insulin dose necessary to reduce the user's blood glucose level below a threshold level or to a target level and automatically deliver the dose. Alternatively, the system can automatically suggest a change in therapy such as an increased insulin basal rate or delivery of a bolus, but can require the user to accept the suggested change prior to delivery. If the CGM data indicates that the user has a low blood glucose level or hypoglycemia, the system can, for example, automatically reduce a basal rate, suggest to the user to reduce a basal rate, automatically deliver or suggest that the user initiate the delivery of an amount of a substance such as, e.g., a hormone (glucagon) to raise the concentration of glucose in the blood, suggest that the user, e.g., ingest carbohydrates and/or automatically take other actions and/or make other suggestions as may be appropriate to address the hypoglycemic condition, singly or in any desired combination or sequence. In some embodiments, multiple medicaments can be employed in such a system such as a first medicament, e.g., insulin, that lowers blood glucose levels and a second medicament, e.g., glucagon, which raises blood glucose levels.

Communication links 24, 35 are illustratively wireless, such as a radio frequency ("RF") or other suitable wireless frequency, in which data and controls are transmitted via electromagnetic waves between sensor 16, therapy delivery device 31, and management device 26. Bluetooth® is one exemplary type of wireless RF communication system that uses a frequency of approximately 2.4 Gigahertz (GHz). Another exemplary type of wireless communication scheme uses infrared light, such as the systems supported by the Infrared Data Association® (IrDA®). Other suitable types of wireless communication may be provided. Furthermore, each communication link 24, 35 may facilitate communication between multiple devices, such as between glucose sensor 16, computing device 26, insulin pump 31, and other suitable devices or systems. Wired links may alternatively be provided between devices of system 10, such as, for example, a wired Ethernet link. Other suitable public or proprietary wired or wireless links may be used.

Figure 2:
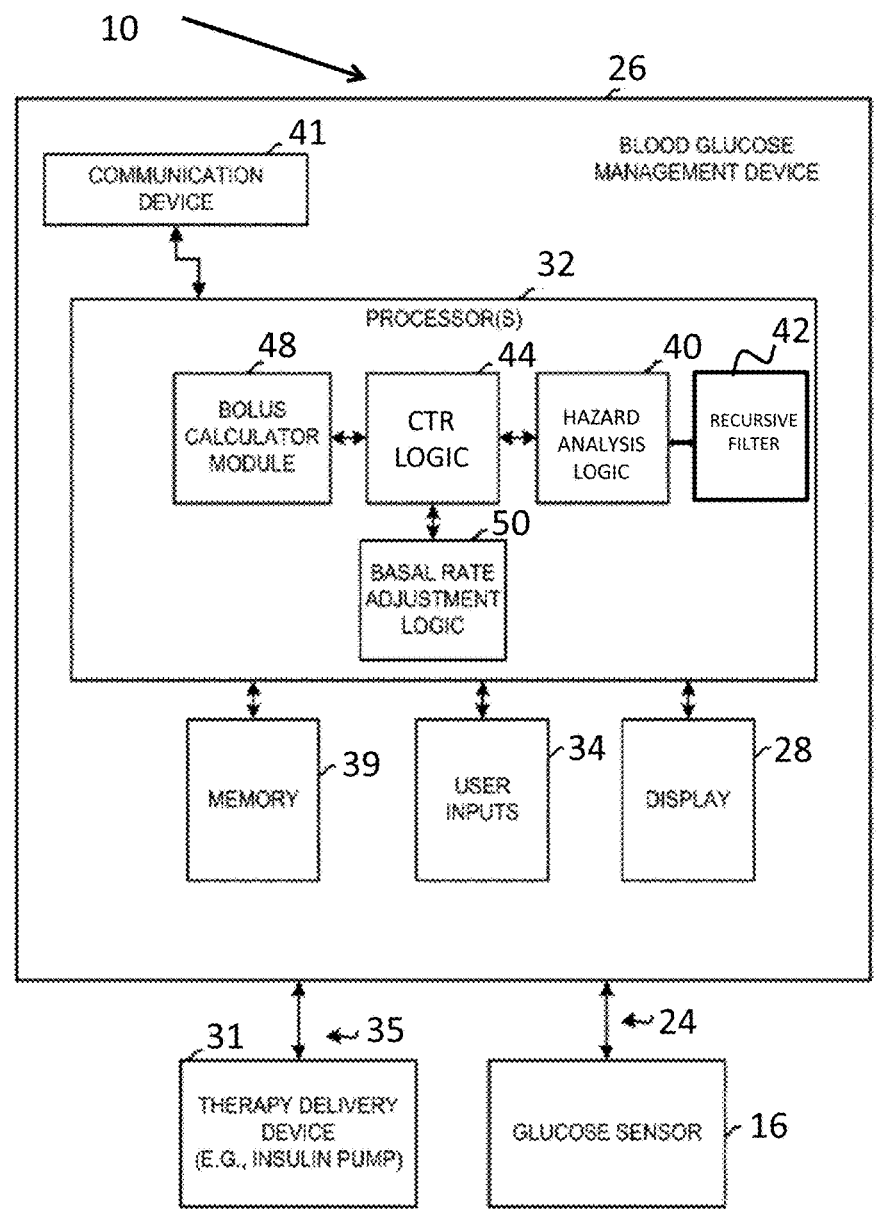
FIG. 2 illustrates an exemplary blood glucose management device, therapy delivery device, and glucose sensor of the CGM system of FIG. 2, the blood glucose management device including a bolus calculator module, control-to-range logic, and basal rate adjustment logic.

FIG. 2 illustrates an exemplary management device 26 of the CGM system 10 of FIG. 2. Management device 26 includes at least one microprocessor or microcontroller 32 that executes software and/or firmware code stored in memory 39 of management device 26. The software/firmware code contains instructions that, when executed by the microcontroller 32 of management device 26, causes management device 26 to perform the functions described herein. Management device 26 may alternatively include one or more application-specific integrated circuits (ASICs), field-programmable gate arrays (FPGAs), digital signal processors (DSPs), hardwired logic, or combinations thereof. While management device 26 is illustratively a glucose monitor 26, other suitable management devices 26 may be provided, such as, for example, desktop computers, laptop computers, computer servers, personal data assistants ("PDA"), smart phones, cellular devices, tablet computers, infusion pumps, an integrated device including a glucose measurement engine and a PDA or cell phone, etc. Although management device 26 is illustrated as a single management device 26, multiple computing devices may be used together to perform the functions of management device 26 described herein.

Memory 39 is any suitable computer readable medium that is accessible by microcontroller 32. Memory 39 may be a single storage device or multiple storage devices, may be located internally or externally to management device 26, and may include both volatile and non-volatile media. Further, memory 39 may include one or both of removable and non-removable media. Exemplary memory 39 includes random-access memory (RAM), read-only memory (ROM), electrically erasable programmable ROM (EEPROM), flash memory, CD-ROM, Digital Versatile Disk (DVD) or other optical disk storage, a magnetic storage device, or any other suitable medium which is configured to store data and which is accessible by management device 26.

The microcontroller 32 may also include additional programming to allow the microcontroller 32 to learn user preferences and/or user characteristics and/or user history data. This information can be utilized to implement changes in use, suggestions based on detected trends, such as, weight gain or loss. The microcontroller 32 can also include programming that allows the device 26 to generate reports, such as reports based upon user history, compliance, trending, and/or other such data. Additionally insulin infusion pump 31 embodiments of the disclosure may include a "power off" or "suspend" function for suspending one or more functions of the device 26, such as, suspending a delivery protocol, and/or for powering off the device 26 or the delivery mechanism thereof. For some embodiments, two or more microcontrollers 32 may be used for controller functions of insulin infusion pump 31, including a high power controller and a low power controller used to maintain programming and pumping functions in low power mode, in order to save battery life.

Management device 26 further includes a communication device 41 operatively coupled to microcontroller 32. Communication device 41 includes any suitable wireless and/or wired communication module operative to transmit and receive data and controls over communication links 24, 35 between device 26 and glucose sensor 16 and insulin pump 31. In one embodiment, communication device 41 includes an antenna 30 (FIG. 1) for receiving and/or transmitting data wirelessly over communication links 24, 35. Management device 26 stores in memory 39 measured glucose results and other data received from glucose sensor 16 and/or insulin pump 31 via communication device 41.

Management device 26 includes one or more user input device(s) 34 for receiving user input. Input device(s) 34 may include pushbuttons, switches, a mouse pointer, keyboard, touchscreen, or any other suitable input device. Display 28 is operatively coupled to microcontroller 32, and may comprise any suitable display or monitor technology (e.g., liquid crystal display, etc.) configured to display information provided by microcontroller 32 to a user. Microcontroller 32 is configured to transmit to display 28 information related to the detected glucose state of the person, the risk associated with the glucose state, and basal rate and bolus information. The glucose state may include the estimated glucose level and the estimated rate-of-change of the glucose level, as well as an estimate of the quality or uncertainty of the estimated glucose level. Moreover, the displayed information may include warnings, alerts, etc. regarding whether the estimated or predicted glucose level of the person is hypoglycemic or hyperglycemic. For example, a warning may be issued if the person's glucose level falls below (or is predicted to fall below) a predetermined hypoglycemic threshold, such as 50 to 70 milligrams of glucose per deciliter of blood (mg/dl). Management device 26 may also be configured to tactilely communicate information or warnings to the person, such as for example by vibrating.

In one embodiment, management device 26 is in communication with a remote computing device (not shown), such as at a caregiver's facility or a location accessible by a caregiver, and data (e.g., glucose data or other physiological information) is transferred between them. In this embodiment, management device 26 and the remote device are configured to transfer physiological information through a data connection such as, for example, via the Internet, cellular communications, or the physical transfer of a memory device such as a diskette, USB key, compact disc, or other portable memory device.

Microcontroller 32 also includes control-to-range logic 44. A control-to-range system reduces the likelihood of a hypoglycemic event or a hyperglycemic event by adjusting insulin dosing only if the PWD's 11 glucose level approaches the low or high glucose thresholds.

Microcontroller 32 includes hazard analysis logic 40 that calculates target return paths from a plurality of initial glucose states to a target glucose state based on cumulative hazard values. The target glucose state is illustratively an optimal or ideal glucose state having no associated hazard or risk, such as a glucose level of 112.5 mg/dl and a glucose rate-of-change of zero, although any suitable target glucose state may be identified. Each target return path is comprised of a plurality of intermediate glucose states that are to be encountered during a transition from the initial glucose state to the target glucose state. Cumulative penalty values associated with the target return paths are stored in memory 76 that may be used as a lookup table. Calculation of cumulative penalty values is discussed infra.

In some embodiments, inaccurate glucose measurements may result from malfunction and/or noise associated with glucose sensor 24. As such, hazard analysis logic 40 analyzes the probability of accuracy of the detected glucose state provided with glucose sensor 24. Hazard analysis logic 40 may use any suitable probability analysis tool to determine the probability of accuracy of a measured glucose result, such as a hidden Markov model. Based on the determined probability of accuracy, hazard analysis logic 40 estimates the glucose level and the glucose rate of change of the person using a recursive filter 42. In particular, recursive filter 42, such as a Kalman filter, for example, weights the detected glucose state, including the glucose level and rate of change, with the determined probability of glucose sensor accuracy. Based on the probability of glucose sensor accuracy, recursive filter 42 calculates an uncertainty measure of the estimated glucose state. The uncertainty measure is indicative of the quality of the estimated glucose state. For a series of detected glucose states, the uncertainty for each state may vary.

Microcontroller 32 of FIG. 2 further includes a bolus calculator module 48 that calculates bolus recommendations and a maximum allowed glucose level of a user which may be displayed to a user via display 28. Management device 26 maintains a record in memory 39 of historical data for the user accumulated over time leading up to the current time. The historical data includes blood glucose history, prescription data, prior bolus recommendations, prior administered boluses, prior basal rates, glucose sensitivity factors for the user's sensitivity to insulin and carbohydrates, blood glucose responses to prior boluses and meal events, other user health and medical data, and the time stamp of each event and data recordation. The history data includes patient recorded information such as meal events, amount of carbohydrates consumed, confirmations of bolus deliveries, medications, exercise events, periods of stress, physiological events, manual insulin injections, and other health events, entered via user inputs 34. Bolus calculator module 48 uses the historical data to more accurately and efficiently determine the recommended insulin bolus and/or carbohydrate amount.

The bolus calculator module 48 determines a recommended bolus, such as an insulin correction bolus or a meal bolus, particular to the user based on the current glucose state, the history data, and user input. A suggested meal bolus (e.g., carbohydrate amount) may be in response to a detected or predicted hypoglycemic condition. A suggested correction bolus of insulin may be in response to the detected glucose exceeding the maximum allowable glucose level. The actual amount of carbohydrates consumed and the actual amount of insulin administered may be confirmed by the user as information entered via user inputs 34 and recorded in memory 39 with other history data. The recommended bolus may be displayed on display 28.

Figure 3:
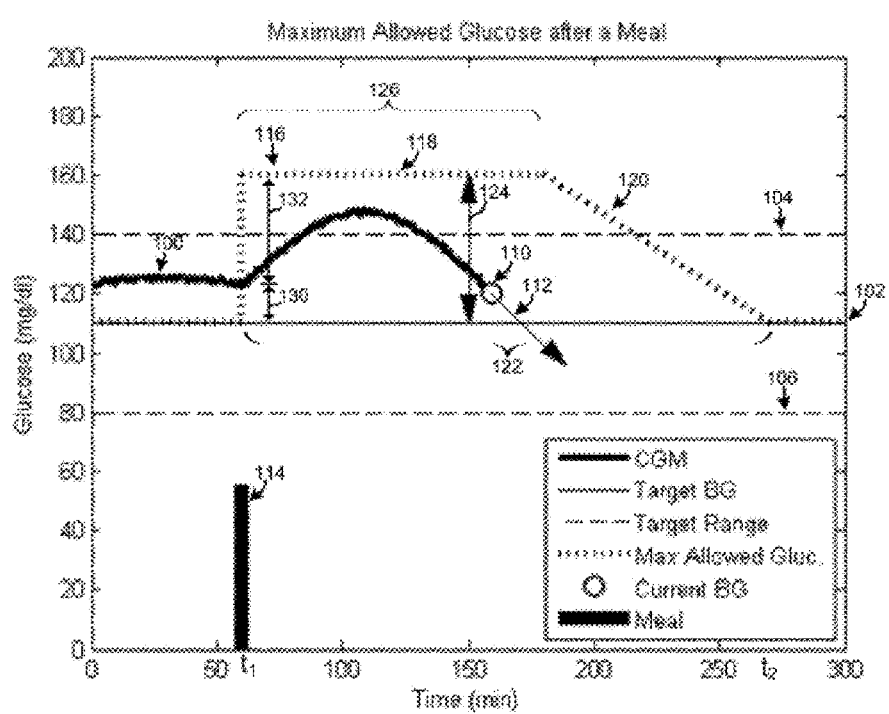
FIG. 3 illustrates a graph plotting an exemplary CGM trace and an adjusted maximum allowed glucose following a meal event.

Referring to FIG. 3, an exemplary CGM trace 100 is illustrated, wherein the x-axis represents time in minutes and the y-axis represents glucose in mg/dl. CGM trace 100 comprises a series of detected glucose levels measured over a period. In the illustrated embodiment, CGM trace 100 represents filtered glucose levels, i.e., glucose levels that are estimated based on the measured glucose levels weighted with the probably of sensor accuracy. A most recent estimated glucose level 110 has an associated negative rate of change indicated with arrow 112. Bolus calculator module 48 determines the target glucose level 102 and a target range of glucose levels indicated with an upper glucose limit 104 and a lower glucose limit 106. For illustrative purposes, target glucose level 102 is 110 mg/dl, upper glucose limit 104 is 140 mg/dl, and lower glucose limit 106 is 80 mg/dl, although other suitable values may be provided. Bolus calculator module 48 may determine target glucose level 102 and limits 104, 106 based at least in part on the user's history data described herein. Management device 26 uses the trending glucose data of CGM trace 100 to recommend corrective action to move the blood glucose towards the target glucose level 102. The target glucose level 102 of FIG. 3 corresponds to the maximum allowed glucose before time $t_1$ and after time $t_2$, i.e., when there has not been any recent meals or correction boluses. Between times $t_1$ and $t_2$, the maximum allowed glucose is adjusted based on a meal event 114 or other suitable events.

At time $t_1$, meal event 114 occurs when the user consumes a meal and enters carbohydrate data into management device 26 indicating the amount of carbohydrates consumed with the meal. In some instances, an insulin bolus is administered at about the time of the meal event 114 to offset the expected increase in glucose levels resulting from the meal. Bolus calculator module 48 determines a projected glucose level rise and a duration of the glucose rise based on the carbohydrates consumed, the insulin correction bolus (if administered), and the user's historical data related to glucose swings following meals and insulin injections. Based on the projected glucose rise, bolus calculator module 48 determines an allowed rise value 124, an offset time value 126, and an acting time value 122. The allowed rise value 124 may be based on other events, such as a glucagon injection, exercise, sleep, driving, or time of day, for example.

The allowed rise value 124 is the amount by which the glucose level of the user may be allowed to increase with respect to the target glucose level 102 as a result of the carbohydrate intake and insulin bolus. In some embodiments, the allowed rise value 124 is the combination of a correction delta glucose value 130 resulting from an insulin bolus and a meal rise value 132 resulting from the meal event 114. The correction delta glucose value 130 is the difference between the current glucose level and the target glucose level 102 at the time of the insulin bolus to allow time for the glucose level to decrease following insulin. As illustrated, the allowed rise value 124 is constant (see line 118) for a first predetermined amount of time after the meal and insulin administration, i.e., offset time 126, and then decreases linearly (see slope 120) following the offset time 126. The total time that the meal and insulin dose have an effect on the bG levels of a patient is the acting time 122. FIG. 3 illustrates a trapezoid-shaped graph 116 of the allowed rise value 124 accounting for the effect of a dose of insulin and meal event.

The maximum allowed glucose increases based on allowed rise value 124 and follows plot 116 of FIG. 3. As such, bolus calculator module 48 expands the range of allowable glucose levels after a meal event for the duration of the acting time 122 according to plot 116. The allowed rise value 124 illustratively has an initial height of 50 mg/dl, but could have other suitable heights based on the meal size, the insulin, and the user's typical reactions to boluses from the historical data. In some embodiments, for meal events above a threshold amount of carbohydrates, the meal rise value 132 is fixed. As one example, the offset time 126 is about two hours, and the acting time 122 is about three to five hours, depending on the user, the meal size, and the insulin bolus.

Referring again to FIG. 2, management device 26 further includes basal rate adjustment logic 50 operative to calculate and adjust a basal rate based on the current glucose state and the risk associated with the current glucose state. Management device 26 transmits an adjustment to the basal rate in a control signal to insulin pump 31 via communication link 35, and insulin pump 31 adjusts the current insulin basal rate based on the adjustment. Alternatively, the adjusted basal rate may be displayed to the user, and the user manually adjusts the basal rate of insulin pump 31. In one or more embodiment, the adjustment is a percent reduction to the initial, unadjusted or nominal basal rate based on a risk of hypoglycemia or a percent increase to the initial, unadjusted or nominal basal rate based on risk of hyperglycemic conditions.

The basal rate adjustment logic 50 determines whether the basal rate is to be adjusted. If an adjusted basal rate is proper, basal rate adjustment logic 50 calculates an adjusted basal rate and management device 26 transmits a control signal to insulin pump 31 to cause insulin pump 31 to deliver insulin at the adjusted basal rate. Alternatively, management device 26 may display the adjusted basal rate to the user to prompt the user for manual adjustment of the insulin pump 31. In some embodiments, the implementation of the adjusted basal rate may be overridden by the user via manual control of the insulin pump 31.

However, because CGM devices estimate blood glucose levels from analyzing interstitial plasma or fluid rather than blood from, e.g., a finger stick, CGM devices generally provide delayed and/or inexact blood glucose monitoring. To ensure that a CGM device is estimating the person with diabetes' 11 true glucose level as reliably and accurately as possible, such devices require a user to perform calibrations with a peripheral blood sample on a repeating basis. The calibration blood sample is then used to compare the user's actual blood glucose level with the blood glucose levels determined by the glucose sensor 16 of the CGM system 10. Such calibration, however, is only done periodically, such as every 12 hours. Embodiments of the present invention therefore incorporate solutions for mitigating the risk of automatically dosing insulin or other medicament to patients based on potentially inaccurate CGM data.

The indirect measurement of blood glucose levels with a CGM device necessitates inclusion of failsafes in the control-to-range algorithm to guard against unreliable increases or decreases in basal insulin rates. Inaccuracies in the blood glucose monitoring from the CGM device may be the result of an inaccurate CGM calibration as a result of drift or other error. The calibration error may cause the glucose sensor 16 of the CGM system 10 to have a bias greater than the current true blood glucose level. Similarly, a calibration error may cause the CGM to have a bias less than the current true blood glucose level. Additionally, an error with the sensor in the GCM device may provide false or incorrect readings for the blood glucose levels. For example, a sensor error may cause the CGM to no longer respond to changes in blood glucose and remain artificially low or artificially high.

Additionally, changes in insulin sensitivity of the PWD may necessitate inclusion of failsafes in the control-to-range algorithm to guard against unreliable increases or decreases in basal insulin rates.

Figure 4:
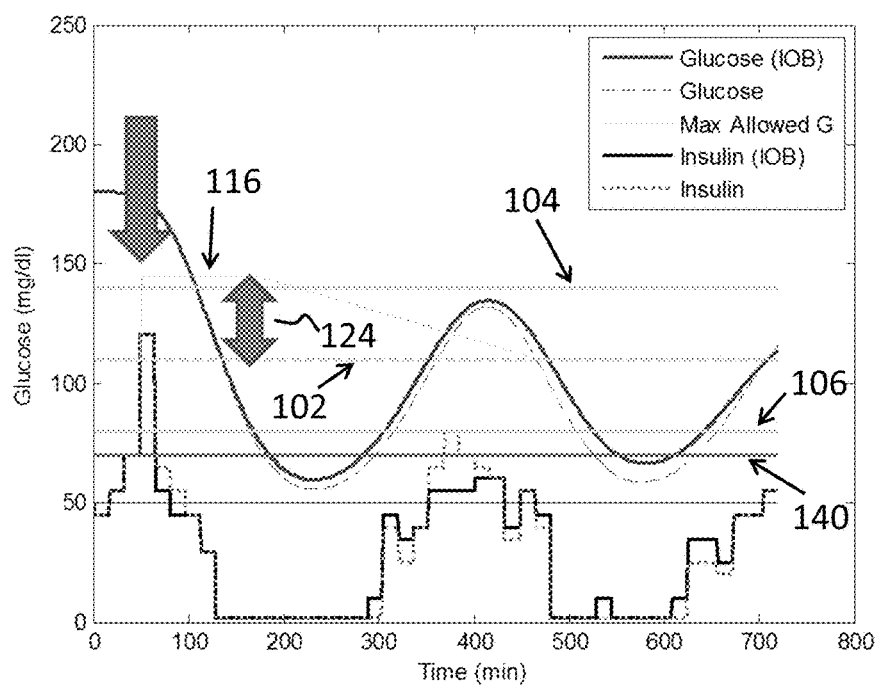
FIG. 4 illustrates a graph plotting an exemplary CGM trace and an adjusted maximum allowed glucose with implementation of a failsafe according to one or more embodiments shown and described herein.

Referring now to FIG. 4, in further embodiments, the CGM system 10 treats increases in the basal rate of insulin as a bolus and inputs the bolus into the bolus calculator module 48 records only if the increase on the basal rate is greater than a predetermined threshold 140. For example, if the basal rate is increased to 1.3× the nominal basal rate, the increased basal rate is treated as a bolus and input into the bolus calculator module 48 records. Other thresholds are contemplated including, for example, 1.1× the nominal basal rate, 1.2× the nominal basal rate, 1.4× the nominal basal rate, 1.5× the nominal basal rate, and 2× the nominal basal rate. The threshold may be determined based on the individual physiological characteristics of the PWD and/or the value of the nominal basal rate. Referring to FIG. 4, the basal rate is temporarily increased to a value greater than the threshold 140. The temporary increase in the basal rate is treated as a correction bolus which causes a trapezoidal rise in the maximum allowed glucose 116.

It is important for the bolus calculator module 48 to know about additional insulin delivered by the CTR algorithm when calculating a correction bolus. When the temporary basal rate (TBR) is above 100% then it could be considered as corrective insulin. However, treating any value above 100% as corrective insulin limits the ability of the controller to respond to legitimate decreases in insulin sensitivity. Therefore a threshold is set such that the TBR percentage is treated as a correction bolus if it exceeds a defined threshold. In one or more embodiments, if the calculated TBR is greater than $TBR_{IOB}$ the insulin that exceeds 100% is treated as a correction bolus. $TBR_{IOB}$ represents a temporary basal rate threshold where the extra basal rate gets handles as a correction bolus. In various embodiments the value of the $TBR_{IOB}$ is set from 130% to 150%. The correction bolus is defined by the following equation:

$$I_{corr} = (TBR-100\%)*BR*TBR_{duration}. \quad (1)$$

where BR represents the nominal basal rate and $TBR_{duration}$ represents the duration of the TBR. When the $I_{corr}$ is delivered as a corrective bolus, the TBR is adjusted to 100%.

Figure 5A:
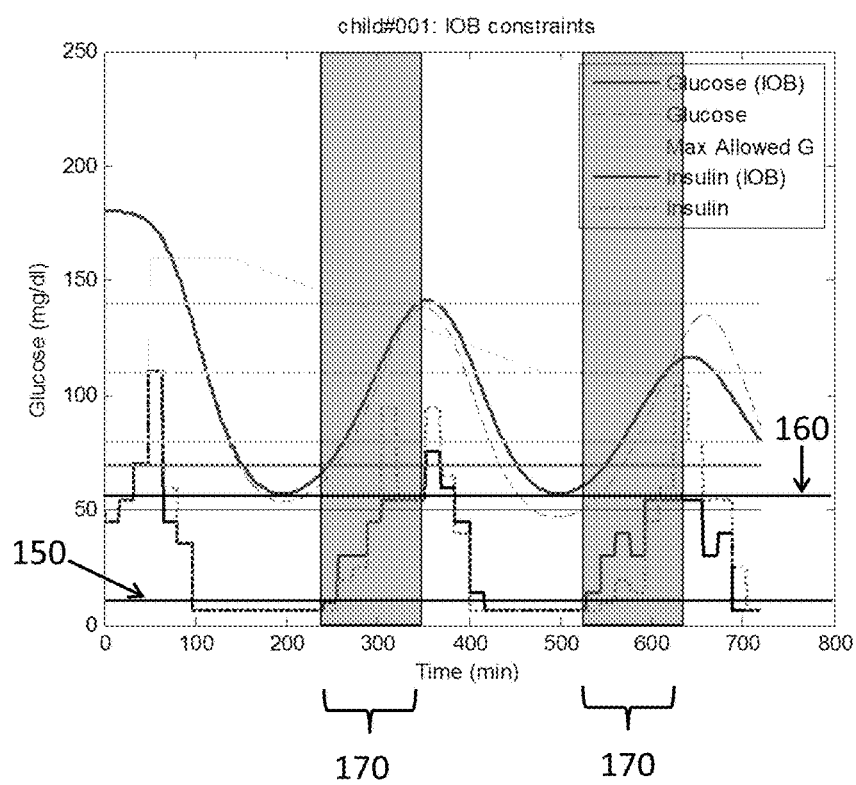
FIG. 5A illustrates a graph plotting an exemplary CGM trace and an adjusted maximum allowed glucose with implementation of a failsafe according to one or more embodiments shown and described herein.

Referring now to FIG. 5A, in further embodiments, if the basal rate is reduced below a threshold 150, the control-to-range algorithm is prevented from increasing the basal rate to a value above a limiting nominal basal rate 160 for a specified period of time 170. The risk of a hypoglycemic event is increased following a previous hypoglycemic event. This constraint helps to address this increase in risk. The lock is triggered by two consecutive time periods with a recommended TBR below a defined threshold 150. This may occur when the glucose value actually goes into the hypo region or by an extreme rate-of-change. Once this lock has been triggered, the TBR value is limited to 110% for a specified amount of time. For example, if the basal rate is reduced to below 0.2× the nominal basal rate the control-to-range algorithm is prevented from increasing the basal rate to above 1.1× the nominal basal rate for 2 hours. Other thresholds 150 are contemplated including, for example, 0.1× the nominal basal rate, 0.3× the nominal basal rate, 0.05× the nominal basal rate, and a basal rate of zero. Additional limiting nominal basal rates are contemplated including, for example, 0.8× the nominal basal rate, 0.9× the nominal basal rate, 1.0× the nominal basal rate, 1.2× the nominal basal rate, and 1.3× the nominal basal rate. Further, additional periods of time where the basal rate is limited are contemplated including, for example, 0.5 hours, 1 hour, 1.5 hours, and 2.5 hours. The threshold 150, limiting nominal basal rate 160, and/or the period of time where the basal rate is limited 170 may be determined based on the individual physiological characteristics of the PWD 11 and/or the value of the nominal basal rate.

In one or more embodiments, as long as the TBR value remains at or below the threshold 150 the lock window 170 is reset. In further embodiments, if the lock has been set and the recommended TBR rate is below $TBR_{lock}$ and greater than 0% with less than a secondary lock period remaining on the lock, then the lock window duration is set to the secondary lock period. $TBR_{lock}$ is a temporary basal rate threshold for transitioning from an initial lock period to the secondary lock period. For example, $TBR_{lock}$ may be set as 90%, the initial lock period may be 120 minutes. and the secondary lock period may be 60 minutes. As such, if the lock has been set and the recommended TBR rate is below 90% and greater than 0% with less than 60 minutes remaining on the lock, then the lock window duration is reset to 60 minutes. This ensures that after a hypoglycemic event the insulin is not increased for at least the length of the secondary lock period after recovering from the hypoglycemic event.

Figure 5B:
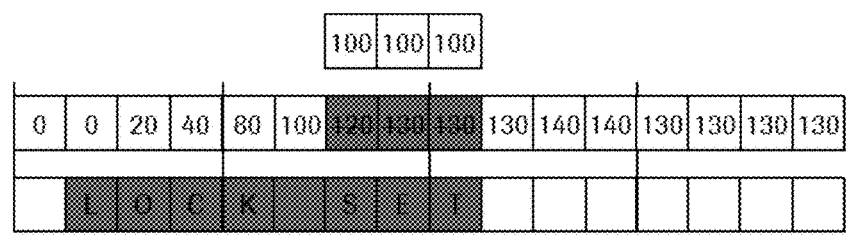
FIGS. 5B and 5C illustrate basal insulin rate increase lock after a hypoglycemic event.
Figure 5C:
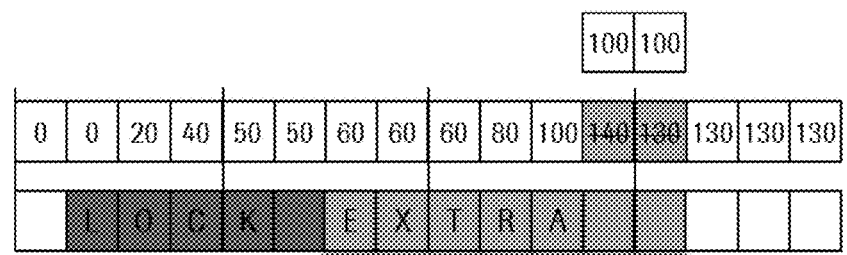

With reference to FIGS. 5B and 5C, the shifting lock periods are illustrated. FIG. 5B illustrates an example where the lock is set when the second 15 minute interval has a TBR of 0%. The lock window is set to 120 minutes. Toward the end of the lock window the system recommends TBRs of 120%, 130%, and 130%. These occur during the lock window and are adjusted down to 100%. After the lock window, the TBR is allowed to increase to values to above 100%. FIG. 5C illustrates an example where the TBR increases gradually after the lock window is triggered. This causes extra time to be added to the lock window (EXTRA). When the second 0% TBR is recommended the lock is set to 120 minutes. When there is less than 60 minutes remaining the TBR recommendation is 60% which is below the $TBR_{lock}$ threshold. This causes an additional 60 minutes to be added to the lock window.

In one or more embodiments, the basal multiplier is limited for a PWD based on their current basal rate and insulin sensitivity factor. For some PwDs the max allowed TBR (TBR$_{MAX}$) should be set to a value lower than 250% or the default setting for TBR$_{MAX}$. These individuals are characterized by having a large glucose correction equivalent of their basal rate (G$_{br}$). This is calculated by multiplying the hourly basal rate (BR) by the insulin sensitivity (IS). For example an individual with a nominal basal rate of 0.9 IU/hr and an insulin sensitivity of 50 mg/dl/IU would have a glucose correction equivalent of 45 mg/dl. PwD with a G$_{br}$ above a threshold (G$_{brT}$) could benefit from a lowered TBR$_{MAX}$. In one or more embodiments, the G$_{brT}$ is set at 150 mg/dl. It will be appreciated that the G$_{brT}$ may be set at values above or below 150 mg/dl as specific PwD circumstances warrant. A temporary basal rate limit (TBR$_{limit}$) to provide a reduced TBR$_{MAX}$ is defined by the following equation:

$$TBR_{limit} = \min\left(TBR_{MAX}, \frac{G_{brT}}{BR*IS} * TBR_{MAX}\right). \quad (2)$$

Similarly to the incremental basal rate multiplier, the temporary basal rate limit may be incremented to the closest TBR increment. The TBR$_{limit}$ is incremented to the closest TBR increment as defined by the following equation:

$$TBR_{inc\ limit} = \min\left(\max\left(\text{round}\left(\frac{TBR_{limit}}{10}\right)*TBR_{inc}, 100\right), 250\right). \quad (3)$$

Figure 6:
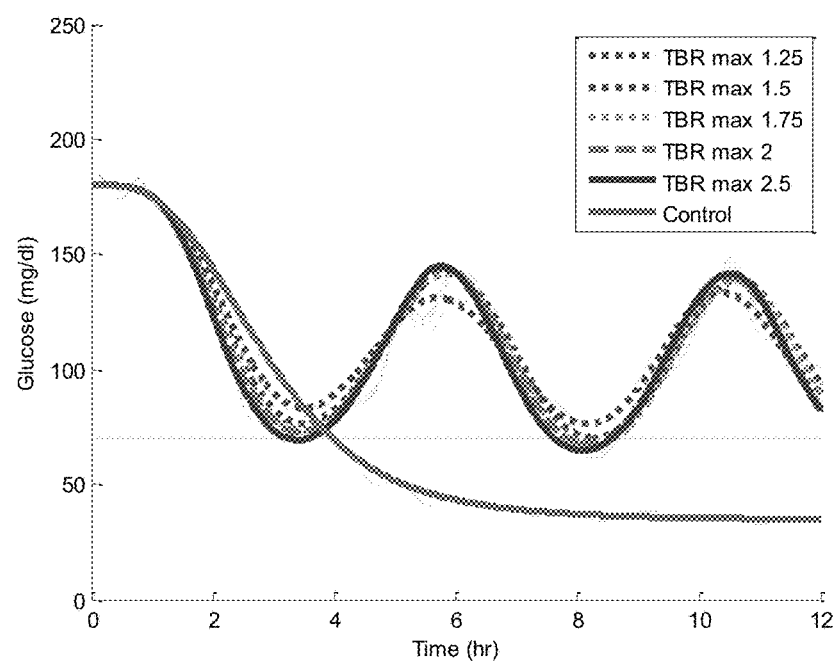
FIG. 6 illustrates a reduction in glucose oscillations upon implementation of treating temporary basal rate increases as a bolus.

The glucose correction equivalent was calculated for 30 simulated PwDs. The simulated subjects numbered 21 and 24 showed an oscillating behavior when their insulin sensitivity was increased. With reference to FIG. 6, an example of this behavior for subject number 24 is illustrated. In this scenario the basal rate was increased by a factor of 1.5 to induce hypoglycemia and the CTR algorithm was turned on to mitigate the effects. Simulations were repeated with different values for the max allowed TBR value ranging from 125% to 250%. The lower values for the max allowed TBR value have a lower magnitude of the oscillations demonstrating the benefit of implementing a TBR$_{limit}$ for PwD with a G$_{br}$ above the G$_{brT}$.

In a further embodiment, the control-to-range algorithm is evaluated on a 15 minute cycle. The amount that the control-to-range algorithm may increase the basal rate multiplier during each evaluation period is limited by a maximum basal multiplier delta. For example, if the current basal rate multiplier is 1.1× of the nominal basal rate then during the next time period the basal rate multiplier may only be increase to 1.6× if the maximum basal multiplier delta is set to 0.5. Other the maximum basal multiplier deltas are contemplated including, for example, 0.2, 0.4, 0.8, 1.0, and 1.5. The maximum basal multiplier delta may be determined based on the individual physiological characteristics of the PWD and/or the value of the nominal basal rate.

In one or more embodiments, the control-to-range algorithm is not utilized when there has been a recent meal. This constraint may be implemented by limiting the maximum allowed basal multiplier if the maximum allowed glucose is greater than the target glucose level. This implementation would also limit the control-to-range algorithm after a correction bolus or manual bolus is administered.

In one or more embodiments, the allowed basal insulin increase is limited based on recent basal increase history. The basal increase history may be obtained from the historical data stored in memory 39 of management device 26. As implemented, if the sum of basal rate increases over a defined time span is greater than the insulin equivalent of an allocation of rescue carbohydrates, then the allowed basal increase is limited. For example, if the sum of basal rate increases over the preceding 1 hour time span is greater than the insulin equivalent of 16 grams of rescue carbohydrates, then the allowed basal increase is limited. Other defined time spans for summing basal rate increases are contemplated including, for example, 15 minutes, 30 minutes, 45 minutes, 1.5 hours, 2 hours, and 4 hours. Additional rescue carbohydrate insulin equivalents are also contemplated including, for example, 8 grams of rescue carbohydrates, 12 grams of rescue carbohydrates, 20 grams of rescue carbohydrates, 24 grams or rescue carbohydrates, and 28 grams of rescue carbohydrates. The defined time span for basal rate increase summing, the rescue carbohydrate insulin equivalent limit, and/or the allowed basal increase limit may be determined based on the individual physiological characteristics of the PWD and/or the value of the nominal basal rate.

In one or more embodiments, the bolus calculator module 48 processes bolus records to detect if an over-correction bolus is delivered. An over-correction bolus is a correction bolus that is greater than the recommended correction bolus. If the bolus calculator module 48 detects an over-correction bolus, a portion of the over-correction bolus is converted into a hypo shift to make the CTR algorithm more sensitive to falling glucose. In this case the excess bolus, the amount greater than the recommended correction bolus, is converted to a glucose adjustment using the insulin sensitivity factor, acting time, and offset time to define a trapezoid following the delivery of the over-correction. The glucose adjustment may be reduced by a fixed amount which may be equal to the distance between the glucose target and the lower glucose target. This provides a bolus buffer where the glucose is not adjusted unless the over-correction bolus will result in a drop below the lower glucose target. In a more risk-adverse scenario the bolus buffer can be set to zero, such that any correction to a value below the target glucose is considered an over-correction. The glucose adjustment is applied as a hypo shift when calculating the risk of a glucose state. This increases the system safety following a correction bolus. The glucose adjustment is then reduced by the glucose equivalent of any reduction in basal rate following the over-correction. The glucose adjustment may be adjusted based on the difference between the expected insulin delivery following the over-correction and the actual insulin delivery following the over-correction. If less insulin was delivered than would nominally be delivered following determination of the over-correction the reduction in insulin is considered removed insulin.

Figure 7:
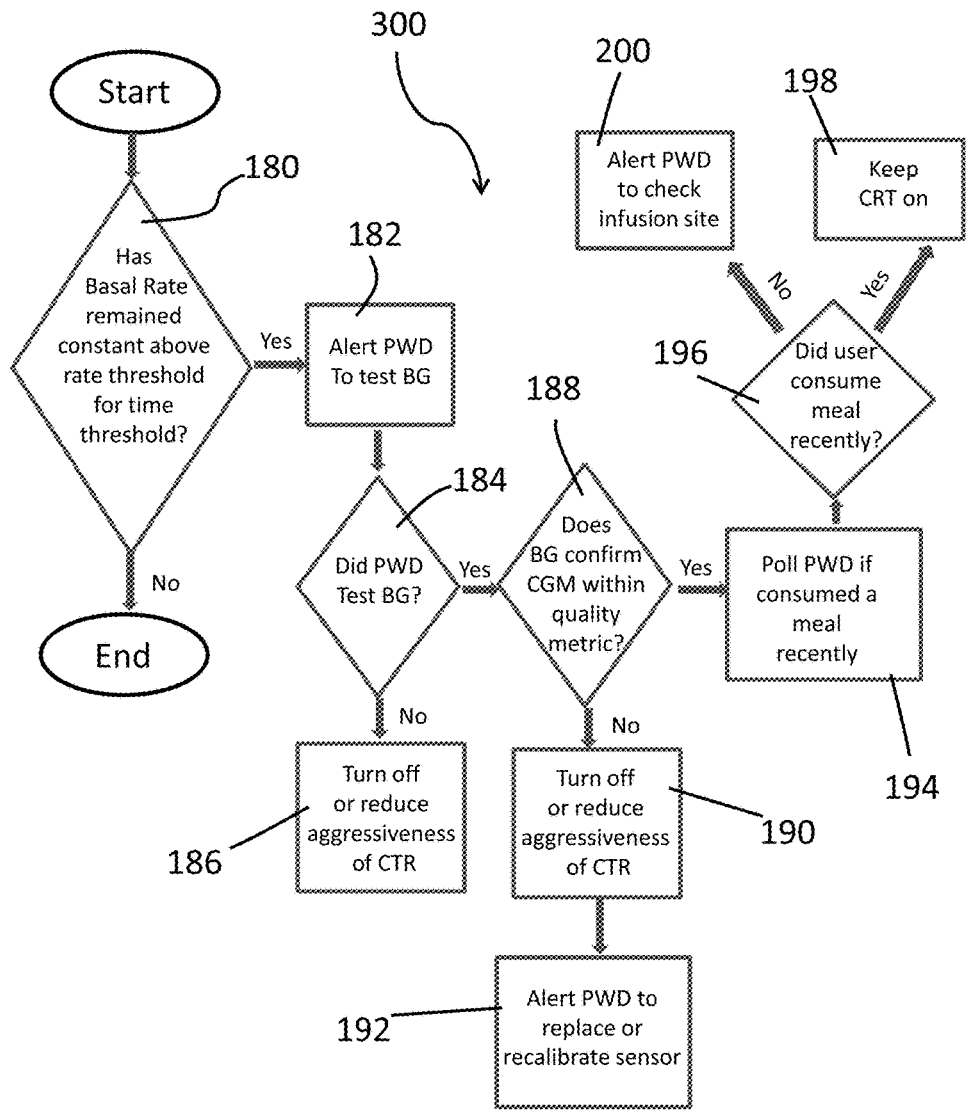
FIG. 7 illustrates a flow chart of an exemplary detailed method of operation of implementation of a failsafe according to one or more embodiments shown and described herein.

Referring to FIG. 7, a flow diagram 300 of an exemplary constraint acting as a failsafe of the control-to-range algorithm is illustrated for verifying the validity of the CGM system 10 blood glucose readings. At block 180 the validity of the CGM system 10 blood glucose readings are verified if the basal insulin rate remains constant above a rate threshold for a sustained period of time exceeding a time threshold. For example, at block 182, if the basal insulin rate remains constant above 110% of the nominal basal rate for a period of time exceeding 2 hours the PWD 11 is alerted to test their blood glucose to confirm the CGM value. Other rate thresholds are contemplated including, for example, 105% of the nominal basal rate, 115% of the nominal basal rate, 120% of the nominal basal rate, and 125% of the nominal basal rate. Additional time thresholds are also contemplated including, for example, 3 hours, 4 hours, the offset time, and the acting time.

At block 184, the microcontroller 32 checks to determine if the PWD 11 follows through with the request to test their blood glucose of block 182. If the PWD 11 does not check their blood glucose, the control-to-range is turned off or the aggressiveness is reduced as illustrated in block 186. If the PWD 11 complies with the instructions to test their blood glucose, the microcontroller 32 queries whether the blood glucose measurement confirms the CGM within a quality metric as illustrated in block 188. For example, the microcontroller 32 verifies that blood glucose measurement and the CGM value agree within +/−20%. Other quality metric are contemplated including, for example, 105% of the nominal basal rate, 115% of the nominal basal rate, 120% of the nominal basal rate, and 125% of the nominal basal rate.

At block 190, the control-to-range is turned off or the aggressiveness is reduced if the CGM data quality check of block 188 fails to confirm agreement between the blood glucose measurement and the CGM measurements. At block 192, the control-to-range is turned back on and/or the aggressiveness is increased back to nominal if the CGM sensor is replaced or recalibrated and confirmed to be accurate.

If the CGM data quality check of block 188 confirms agreement between the blood glucose measurement and the CGM measurements, at block 194 the CGM system 10 polls the PWD 11 regarding if he has consumed a recent meal. The microcontroller 32 receives the PWD's 11 response at block 194 and acts accordingly. Specifically, at block 198, the control-to-range is kept on if the PWD 11 recently consumed a meal. The consumption of a recent meal justifies and explains the increased basal insulin rate for the time threshold. Conversely, at block 200, the PWD 11 is alerted to check the infusion site if the PWD 11 did not consume a meal recently. If the blood glucose measurement and the CGM measurement are in agreement and the patient did not recently consume a meal, but the basal insulin rate is consistently higher than nominal, that is indicative of the insulin no properly reaching the patient and/or the patient not responding to the insulin as expected.

Experimental Results

A simulation study was performed to demonstrate the effectiveness of the control-to-range failsafes. The study comprised the modeled blood glucose of 30 simulated subjects over a 5 day period with typical meals and carbohydrate estimation errors. The control-to-range algorithm without any of the failsafe constraints was applied to obtain a baseline modeled blood glucose of the 30 simulated subjects over a 5 day period (Baseline Simulation). The control-to-range algorithm with the failsafe constraints of the present disclosure implemented was applied to obtain a comparative modeled blood glucose of the 30 simulated subjects over a 5 day period (Failsafe Simulation).

Figure 8:
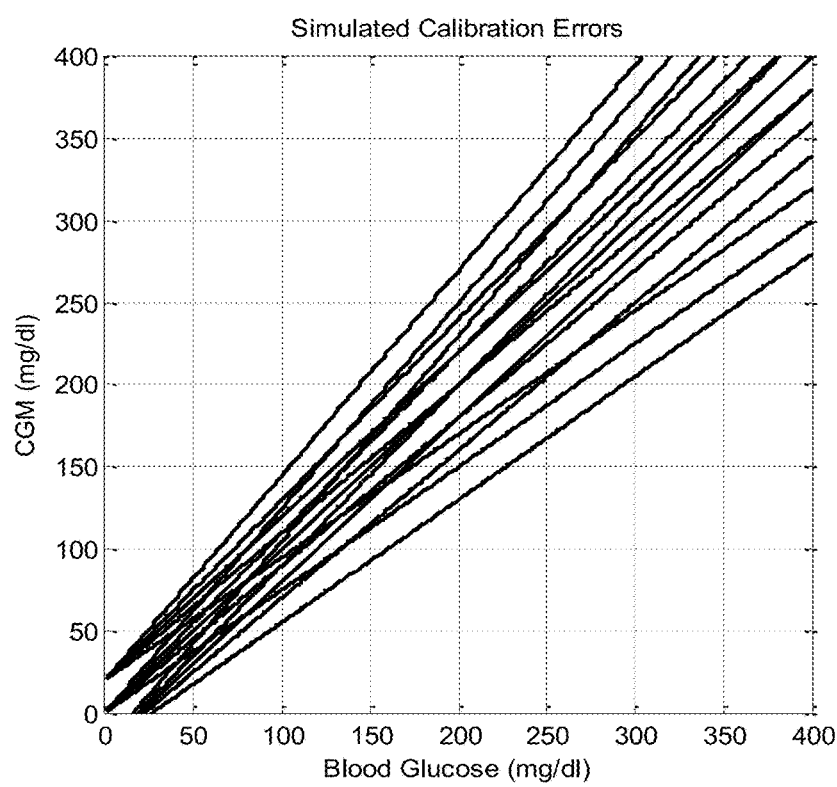
FIG. 8 illustrates a graph plotting simulated calibration errors of the CGM.

Simulated calibration errors were added to the CGM data generated during the simulation of the 30 subjects. The simulated calibration errors represented +/−20 mg/dl absolute error combined with +/−25% and +/−10% relative errors. Simulations were also performed with no added absolute or relative errors. FIG. 8 illustrates the range of added error between the simulated true blood glucose and the simulated CGM blood glucose measurements.

In a control group which did not include any control-to-range algorithm, there were 34 hypoglycemic events below 70 mg/dl.

The incidence of hypoglycemic events below 70 mg/dl was recorded for both the baseline simulation representing the control-to-range algorithm without the failsafe constraints of the present disclosure implemented and the failsafe simulation representing the control-to-range algorithm with the failsafe constraints of the present disclosure implemented. The findings are presented in Tables 1 and 2 respectively infra.

TABLE 1

Baseline Simulation (control-to-range algorithm without the failsafe constraints)

|  | 0.75 | 0.9 | 1 | 1.1 | 1.25 |
| --- | --- | --- | --- | --- | --- |
| −20 mg/dl | 0 events | 1 events | 6 events | 9 events | 11 events |
| 0 mg/dl | 0 events | 5 events | 8 events | — | 27 events |
| 20 mg/dl | 3 events | 8 events | 16 events | 27 events | 65 events |

TABLE 2

Failsafe Simulation (control-to-range algorithm with the failsafe constraints)

|  | 0.75 | 0.9 | 1 | 1.1 | 1.25 |
| --- | --- | --- | --- | --- | --- |
| −20 mg/dl | 0 events | 1 events | 4 events | 6 events | 8 events |
| 0 mg/dl | 0 events | 3 events | 7 events | — | 15 events |
| 20 mg/dl | 4 events | 8 events | 12 events | 16 events | 29 events |

In the worse case with an absolute error of +20 mg/dl and a relative error of +25% the baseline simulation representing implementation of the control-to-range algorithm without the failsafe constraints of the present disclosure implemented, 65 hypoglycemic events were recorded during the 5 day simulation. Conversely, the improvement from implementation of the control-to-range algorithm the failsafe constraints of the present disclosure in the failsafe simulation is illustrated with the drop to 29 hypoglycemic events. Table 3, presented infra, provides relative number of hypoglycemic events for the failsafe simulations compared to the baseline simulations. Implementation of the failsafes of the present disclosure improved the relative performance of the control-to-range in avoiding hypoglycemic events. No simulated calibration error sector resulted in an increase in the number of hypoglycemic events and some sectors indicated improvements representing more than a 50% reduction in hypoglycemic events (absolute error of +20 mg/dl and a relative error of +25%)

TABLE 3

Comparative reduction from implementation of failsafes (hypoglycemic events for failsafe simulation/hypoglycemic events for baseline simulation)

|  | 0.75 | 0.9 | 1 | 1.1 | 1.25 |
| --- | --- | --- | --- | --- | --- |
| −20 mg/dl | 1 | 1 | 0.67 | 0.67 | 0.73 |
| 0 mg/dl | 1 | 0.6 | 0.88 | — | 0.56 |
| 20 mg/dl | 0.75 | 1 | 0.75 | 0.59 | 0.45 |

For further and alternative descriptions for determining the basal rate adjustment, see U.S. patent application Ser. No. 14/229,016, filed on Mar. 28, 2015, entitled "System and Method for Adjusting Therapy Based on Risk Associated with a Glucose State," the entire disclosure of which is incorporated by reference herein. For further description of calculating the target return paths and calculating risk metrics, see U.S. patent application Ser. No. 13/645,198, filed on Oct. 4, 2012, entitled "System and Method for Assessing Risk Associated with a Glucose State," the entire disclosure of which is incorporated by reference herein. For further description of the probability analysis tool, the recursive filter, the uncertainty calculation, and other probability and risk analysis functionalities of computing device 26, see U.S. patent application Ser. No. 12/693,701, filed on Jan. 26, 2010, entitled "Methods and Systems for Processing Glucose Data Measured from a Person Having Diabetes," and U.S. patent application Ser. No. 12/818,795, filed on Jun. 18, 2010, entitled "Insulin Optimization Systems and Testing Methods with Adjusted Exit Criterion Accounting for System Noise Associated with Biomarkers," the entire disclosures of which are incorporated by reference herein. For further description of the bolus calculator module 48, see U.S. patent application Ser. No. 13/593,557, filed on Aug. 24, 2012, entitled "Handheld Diabetes Management Device with Bolus Calculator," and U.S. patent application Ser. No. 13/593,575, filed on Aug. 24, 2012, entitled "Insulin Pump and Methods for Operating the Insulin Pump," the entire disclosures of which are incorporated by reference herein.

It should now be understood that the methods and systems described herein may be used to estimate the glucose level of a person having diabetes and utilize a control-to-range algorithm to adjust the glucose level of a person having diabetes. Furthermore, the methods and systems described herein may also be used to provide fail safes with the control-to-range algorithm to reliably increase insulin basal rates to account for increases in glucose concentration. The methods described herein may be stored on a computer-readable medium which has computer-executable instructions for performing the methods. Such computer-readable media may include compact discs, hard drives, thumb drives, random-access memory, dynamic random-access memory, flash memory, and so forth.

It is noted that recitations herein of a component of the present disclosure being "configured" in a particular way, "configured" to embody a particular property, or function in a particular manner, are structural recitations, as opposed to recitations of intended use. More specifically, the references herein to the manner in which a component is "configured" denotes an existing physical condition of the component and, as such, is to be taken as a definite recitation of the structural characteristics of the component.

While particular embodiments and aspects of the present invention have been illustrated and described herein, various other changes and modifications may be made without departing from the spirit and scope of the invention. Moreover, although various inventive aspects have been described herein, such aspects need not be utilized in combination. It is therefore intended that the appended claims cover all such changes and modifications that are within the scope of this invention.

What is claimed is:

1. A method of determining a basal rate adjustment of insulin in a continuous glucose monitoring system of a person with diabetes, the method comprising:
    receiving, by at least one computing device, a signal representative of at least one glucose measurement;
    detecting, by the at least one computing device, a glucose state of the person based on the signal, the detected glucose state including a glucose level of the person and a rate of change of the glucose level;
    calculating, by the at least one computing device, an adjustment to a basal rate of a therapy delivery device based on a control-to-range algorithm and at least one failsafe constraint to account for changes in the insulin sensitivity of the person with diabetes or inaccurate glucose measurement, wherein the therapy delivery device has a nominal basal rate representing an unadjusted basal rate set for the person with diabetes;
    wherein the failsafe constraint is calculated in accordance with a method selected from the group consisting of:
        (a) calculating bolus recommendations with a bolus calculator, the computing device comprising the bolus calculator, and
            treating increases in the basal rate as a bolus and inputting the bolus into the bolus calculator if the increase is greater than a threshold representing a predetermined multiple of the nominal basal rate;
        (b) determining if the basal rate is at or below a threshold value, and
            limiting the control-to-range algorithm to increasing the basal rate to a limiting nominal basal rate for a specified period of time if the basal rate is at or below the threshold value;
        (c) limiting the amount that the control-to-range algorithm may increase a basal rate multiplier during each evaluation period to a maximum basal multiplier delta;
        (d) determining the sum of basal rate increases over a defined time span,
            determining if the sum of basal rate increases is greater than the insulin equivalent of a predetermined allocation of rescue carbohydrates, and
            limiting the basal rate increase if the sum of basal rate increases is greater than the insulin equivalent;
        (e) determining if the basal rate remains above 1.1× the nominal basal rate for a predetermined period of time,
            alerting the person with diabetes to test their blood sugar and input the tested blood sugar into the continuous glucose monitoring system as an input blood sugar measurement, and
            accessing agreement between the input blood sugar measurement and the detected glucose level of the person with diabetes within a predetermined metric of quality, wherein if the at least one computing device determines the input blood sugar measurement and the detected glucose level of the person with diabetes are not in agreement within the predetermined metric of quality, the control-to-range algorithm is turned off or the aggressiveness is reduced until the sensor in the continuous glucose monitoring system is replaced or the sensor is recalibrated and confirmed to be accurate; and
        (f) combinations thereof.

2. The method of claim 1, further comprising displaying to a user, on a graphical user interface, graphical data representative of the calculated adjustment to the basal rate.

3. The method of claim 1, further comprising transmitting a control signal to instruct the therapy delivery device to adjust the basal rate based on the calculated adjustment.

4. The method of claim 3, wherein the therapy delivery device includes an insulin pump for delivering insulin to the person with diabetes, and the therapy delivery device is in communication with the at least one computing device for receiving the calculated adjustment of the basal rate.

5. The method of claim 1, wherein for failsafe constraint (a) the increase in the basal rate is converted into a bolus for input into the bolus calculator by the at least one computing device in accordance with $$I_{corr} = (TBR - 100\%) * BR * TBR_{duration}$$

where $I_{corr}$ is the correction bolus, TBR is a temporary basal rate, BR is the nominal basal rate, and $TBR_{duration}$ is the duration of the TBR.

6. The method of claim 1, wherein the threshold is 1.3× the nominal basal rate.

7. The method of claim 1, wherein for failsafe constraint (b) the threshold value is 0.2× the nominal basal rate.

8. The method of claim 1, wherein for failsafe constraint (b) the threshold value is zero.

9. The method of claim 1, wherein for failsafe constraint (b) the limiting nominal basal rate is 1.1× the nominal basal rate.

10. The method of claim 1, wherein for failsafe constraint (b) the specified period of time is 2 hours.

11. The method of claim 10, wherein a basal multiplier of the nominal basal rate is limited based on the current basal rate and a person with diabetes' insulin sensitivity factor.

12. The method of claim 11, wherein the limit of the multiplier of the nominal basal rate is determined by the at least one computing device in accordance with $$TBR_{limit} = \min\left(TBR_{MAX}, \frac{G_{brT}}{BR * IS} * TBR_{MAX}\right)$$

where $TBR_{limit}$ is the temporary basal rate multiplier limit, $TBR_{MAX}$ is a maximum temporary basal rate multiplier, $G_{brT}$ is a maximum allowed value for a glucose correction equivalent, BR is the nominal basal rate, and IS is the insulin sensitivity of the person wherein the glucose correction equivalent is calculated by multiplying BR and IS.

13. The method of claim 1, wherein for failsafe constraint (c) the maximum basal multiplier delta is 0.5× the nominal basal rate.

14. The method of claim 1, wherein for failsafe constraint (e) the predetermined metric of quality is agreement within +/−20%.

15. The method of claim 1, wherein for failsafe constraint (b) if the basal rate is reduced to 0% of the nominal basal rate for 2 detecting cycles of the glucose state, the basal rate is prevented from rising above 1.1× the nominal basal rate for 120 minutes.

16. A blood glucose management device configured to determine a basal rate adjustment in a continuous glucose monitoring system of a person with diabetes, the device comprising:
a non-transitory computer-readable medium storing executable instructions; and
at least one processing device configured to execute the executable instructions such that, when executed by the at least one processing device, the executable instructions cause the at least one processing device to:
receive a signal representative of at least one glucose measurement;
detect a glucose state of the person based on the signal, the detected glucose state including a glucose level of the person and a rate of change of the glucose level; and
calculate an adjustment to a basal rate of a therapy delivery device based on a control-to-range algorithm and at least one failsafe constraint to account for changes in the insulin sensitivity of the person with diabetes or inaccurate glucose measurement, wherein the therapy delivery device has a nominal basal rate representing an unadjusted basal rate set for the person with diabetes;
wherein the failsafe constraint is calculated in accordance with a method selected from the group consisting of:
(a) calculating bolus recommendations with a bolus calculator, the computing device comprising the bolus calculator, and
treating increases in the basal rate as a bolus and inputting the bolus into the bolus calculator if the increase is greater than a threshold representing a predetermined multiple of the nominal basal rate;
(b) determining if the basal rate is at or below a threshold value, and
limiting the control-to-range algorithm to increasing the basal rate to a limiting nominal basal rate for a specified period of time if the basal rate is at or below the threshold value;
(c) limiting the amount that the control-to-range algorithm may increase a basal rate multiplier during each evaluation period to a maximum basal multiplier delta;
(d) determining the sum of basal rate increases over a defined time span,
determining if the sum of basal rate increases is greater than the insulin equivalent of a predetermined allocation of rescue carbohydrates, and
limiting the basal rate increase if the sum of basal rate increases is greater than the insulin equivalent;
(e) determining if the basal rate remains above 1.1× the nominal basal rate for a predetermined period of time,
alerting the person with diabetes to test their blood sugar and input the tested blood sugar into the continuous glucose monitoring system as an input blood sugar measurement, and
accessing agreement between the input blood sugar measurement and the detected glucose level of the person with diabetes within a predetermined metric of quality, wherein if the at least one computing device determines the input blood sugar measurement and the detected glucose level of the person with diabetes are not in agreement within the predetermined metric of quality, the control-to-range algorithm is turned off or the aggressiveness is reduced until the sensor in the continuous glucose monitoring system is replaced or the sensor is recalibrated and confirmed to be accurate; and
(f) combinations thereof.

* * * * *